(12) United States Patent  
Wang (10) Patent No.: US 7,281,801 B2
(45) Date of Patent: Oct. 16, 2007

(54) TEAR DYNAMICS MEASURED WITH OPTICAL COHERENCE TOMOGRAPHY

(75) Inventor: Jianhua Wang, Rochester, NY (US)

(73) Assignee: University of Rochester, Rochester, NY (US)

( * ) Notice: Subject to any disclaimer, the term of this patent is extended or adjusted under 35 U.S.C. 154(b) by 293 days.

(21) Appl. No.: 10/941,249

(22) Filed: Sep. 15, 2004

(65) Prior Publication Data

US 2006/0109423 A1 May 25, 2006

(51) Int. Cl.
 *A61B 3/00* (2006.01)
 *A61B 3/10* (2006.01)
 *A61B 6/00* (2006.01)
(52) U.S. Cl. .................. 351/246; 351/205; 600/476
(58) Field of Classification Search ........ 351/205–206, 351/211–212, 246, 221; 600/476, 425
 See application file for complete search history.

(56) References Cited

U.S. PATENT DOCUMENTS

| 4,747,683 | A | * | 5/1988 | Doane ..................... 351/206 |
| 5,491,524 | A | | 2/1996 | Hellmuth |
| 6,137,585 | A | | 10/2000 | Hitzenberger |
| 6,236,459 | B1 | * | 5/2001 | Negahdaripour et al. ... 356/496 |
| 6,447,119 | B1 | * | 9/2002 | Stewart et al. ............. 351/212 |
| 6,588,903 | B2 | | 7/2003 | Rathjen |
| 6,601,956 | B1 | | 8/2003 | Jean et al. |
| 7,113,818 | B2 | * | 9/2006 | Podoleanu et al. ......... 600/476 |
| 7,121,666 | B2 | * | 10/2006 | Tseng et al. ............... 351/206 |

OTHER PUBLICATIONS

L. Jones, et al., "A Novel Method to Determine Tear Prism Height," Association for Research in Vision and Ophthalmology (ARVO), May 2002, Poster.
Jianhua Wang, et al. "Precorneal and Pre-and Postlens Tear Film Thickness measured indirectly with Optical Coherence Tomography," Investigative Ophthalmology & Visual Science, Jun. 2003, vol. 44, No. 6, pp. 2524-2528.
Sunita Radhakrishnan et al., "Real-Time Optical Coherence Tomography of the Anterior Segment at 1310 nm," Arch. Ophthamol., vol. 119, Aug. 2001, pp. 1179-1185.

* cited by examiner

*Primary Examiner*—Scott J. Sugarman
*Assistant Examiner*—DaWayne A Pinkney
(74) *Attorney, Agent, or Firm*—McDermott Will & Emery LLP (57) ABSTRACT

A system and method are provided for measuring the thickness of a tear film layer and the heights of tear menisci around upper and lower eyelids of an eye. A plurality of images are acquired between consecutive blinks the eye using optical coherence tomography (OCT). The images depict the tear film layer and tear menisci as distinct from the cornea of the eye. In an embodiment, a plurality of reflectivity profiles from an OCT image are aligned and averaged. The difference between a first peak and a second peak of the average reflectivity profile is measured to determine the thickness of the tear film layer. The heights of the upper meniscus and the lower meniscus can also be measured from the same OCT image. In an embodiment, thickness measurements from the plurality of OCT images are combined. The measurements can be used to diagnose tear disorders, analyze treatments of dry eye and evaluate artificial tears.

20 Claims, 10 Drawing Sheets

TEAR DYNAMICS MEASURED WITH OPTICAL COHERENCE TOMOGRAPHY

BACKGROUND OF THE INVENTION

1. Field of the Invention

The present invention relates to optical coherence tomography. More specifically, the present invention relates to methods and systems for analyzing the thickness of a tear film layer and the heights of tear menisci around upper and lower eyelids of an eye.

2. Description of the Related Art

Tears secreted by the lacrimal gland spread over the cornea with each blink to form a thin layer (i.e., tear film) and menisci at the upper and lower eyelids. The volume and distribution of the tear film layer and the upper and lower menisci change rapidly between successive blinks. The dynamic variation of the tear film layer and upper and lower menisci plays an important role in visual function, maintenance of corneal integrity and ocular comfort. For example, dry eye syndrome (DES) has been reported to affect functional visual acuity and the performance of routine activities, such as working, reading and driving. DES is characterized by symptoms of ocular dryness and discomfort due. However, there are currently no objective diagnostic criteria for DES and no objective means of evaluating treatment efficacy. Indeed, the dynamic variations of tears remain one of the most neglected areas of ophthalmology.

This neglect is due in part to the difficulty of quantitatively measuring the thickness of the tear film layer. The neglect is also partly due to the difficulty of quantitatively imaging the tear menisci around both upper and lower eyelids during a period of one or more successive blinks when the tear is redistributed around the cornea and upper and lower eyelids. Since the tear film characteristics vary widely from person to person and are strongly influenced by both physiological and environmental conditions, it is difficult to characterize these tear parameters using a single method.

Objective measures of tear film have been elusive for several reasons including the difficulty of achieving acceptable optical resolution of tear film and the fact that tear film is continuously changing due to tear drainage and evaporation. Contact methods for measuring tear volume using, for example, a glass fiber or filter paper are associated with a risk of injury and are not usually applied on human subjects. Further, such methods provide static measurements and do not provide information on how the distribution and volume of tears change over time.

Optical coherence tomography (OCT) is a noninvasive, non-contact imaging technology that has been used to image the anterior segment of the eye, including thickness measurements of the retina and nerve fiber layers. OCT has also been used to measure the thickness of the cornea, epithelium, corneal flap and iris. OCT generates two-dimensional, cross-sectional images from multiple scans of back-scattered light. OCT has good repeatability in the measurement of corneal thickness.

Since tear fluid and ocular structures have different refractive indices, OCT has been used in a limited way to study tears. However, OCT devices previously used to analyze tear film only generate approximately one image per second and are typically reset between images such that only one image can be acquired approximately every twenty seconds. Such slow acquisition rates are not suitable for measuring the rapid changes in tear dynamics.

Further, OCT tear measurements typically measure only one tear parameter at a time. For example, an OCT image typically provides information for only the lower meniscus or for the tear film thickness, but not both. Thus, OCT tear film measurements have not been used to analyze the relationships between tear film thickness and meniscus height around both upper and lower eyelids.

SUMMARY OF THE INVENTION

Thus, it would be advantageous to have a system and technique for measuring rapid changes in tear film dynamics and for non-invasively measuring the tear film thickness, lower meniscus height, and upper meniscus height at the same time.

Accordingly, an embodiment of the invention includes a method of imaging a tear film layer of an eye. The method includes acquiring a plurality of images of the eye between consecutive blinks of the eye. At least one of the images, if displayed, depicts the tear film layer as distinct from the cornea of the eye.

In an embodiment, a method of imaging a tear film layer of an eye includes measuring a differential reflection of the tear film layer and the cornea of the eye at least twice between consecutive blinks. In another embodiment, a method of imaging an eye includes measuring a characteristic of a tear film layer of the eye with an instrument at least twice between consecutive blinks of the eye, wherein the instrument does not physically contact the eye during the measurement.

A system for evaluating a tear film layer of an eye according to an embodiment of the invention includes an optical coherence tomography (OCT) device configured to acquire at least two images of the tear film layer between consecutive blinks of the eye. The system also includes an executable program configured to process the at least two images acquired by the OCT device. The executable program is further configured to determine a thickness of the tear film layer.

In an embodiment, a system for evaluating a tear film layer of an eye includes means for acquiring at least two images of the tear film layer between consecutive blinks of the eye and means for determining a thickness of the tear film layer.

In an embodiment, a diagnostic device is provided that includes an optical coherence tomography system configured to measure a thickness of a tear film layer of an eye at least twice between consecutive blinks of the eye. In addition or in other embodiments, a diagnostic device is provided that includes an optical coherence tomography system configured to measure a height of a tear film meniscus of an eye at least twice between consecutive blinks of the eye.

In an embodiment, a method of imaging an eye includes measuring a thickness of a tear film layer of the eye at least twice between consecutive blinks of the eye. In an embodiment, a method of imaging an eye includes measuring a height of a tear film meniscus of the eye at least twice between consecutive blinks of the eye.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Systems and methods that embody the various features of the invention will now be described with reference to the following drawings.

DETAILED DESCRIPTION OF THE PREFERRED EMBODIMENT

The present invention involves systems and methods for rapidly measuring tear film quality and quantity. Tear film dynamics, including the thickness of the tear film and the heights of upper and lower tear menisci, are measured in real-time in a non-invasive way using OCT images. As used herein, the term "image" has its normal and customary meaning and includes the graphical representation of an object or structure as well as the data that makes up the graphical representation. As described in more detail below, an OCT image according to an embodiment is a rapidly repeatable cross-section of the tear film and the tear menisci around the both eyelids.

In an embodiment of the invention, the OCT tear film dynamic measurements are used to diagnose ocular diseases and disorders or to analyze the effectiveness of treatments for such diseases and disorders. Thus, a wide range of tear film studies can be implemented to tear film and its impact on vision, comfort and ocular integrity in normal and abnormal eyes (e.g. dry eye).

In the following description, reference is made to the accompanying drawings, which form a part hereof and which show, by way of illustration, specific embodiments or processes in which the invention may be practiced. Where possible, the same reference numbers are used throughout the drawings to refer to the same or like components. In some instances, numerous specific details are set forth in order to provide a thorough understanding of the present invention. The present invention, however, may be practiced without the specific details of advantages or with certain alternative equivalent components and methods to those described herein. In other instances, well-known components and methods have not been described in detail so as not to unnecessarily obscure aspects of the present invention.

OCT System

Figure 1:
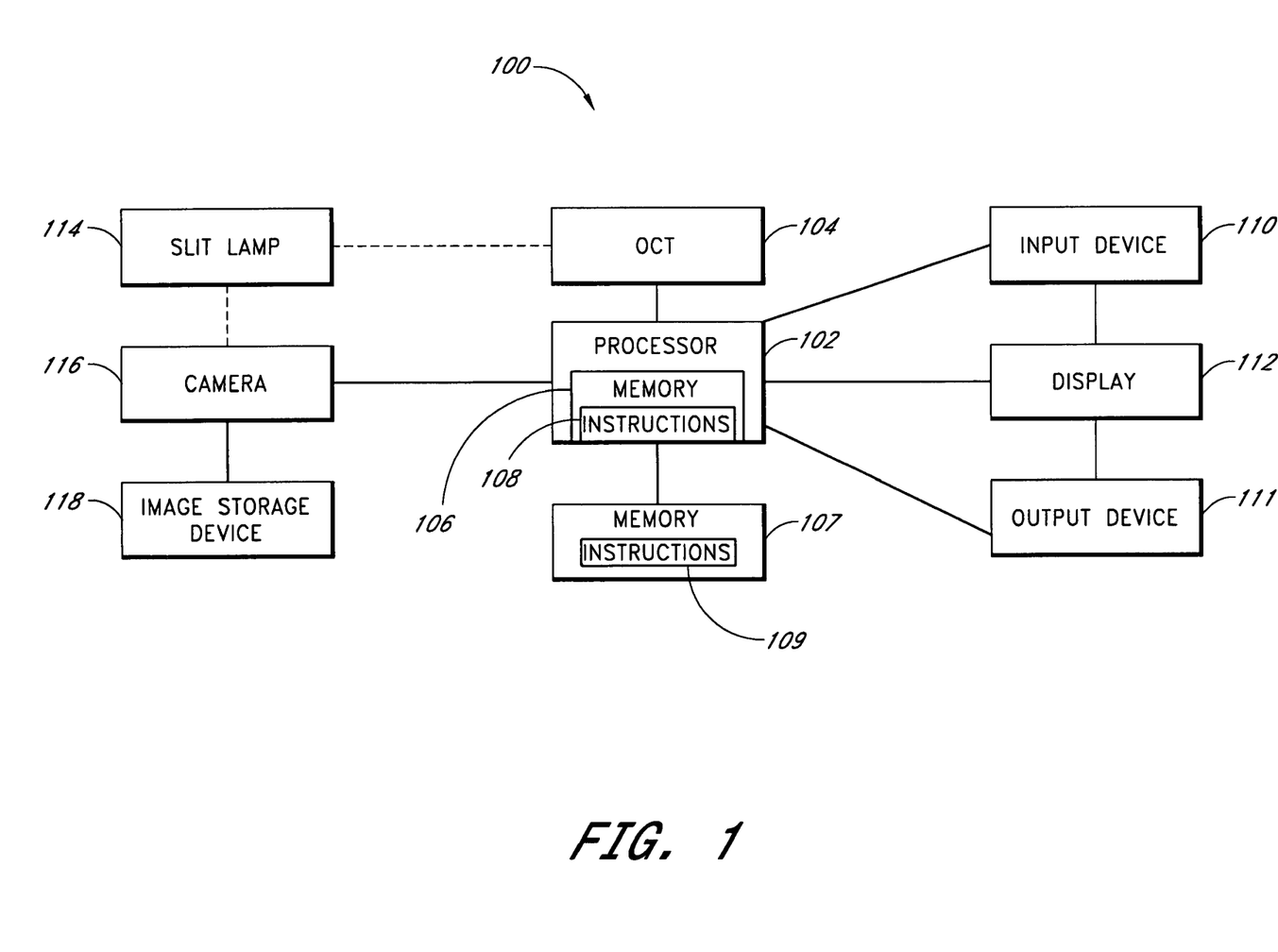
FIG. 1 is a block diagram of a system according to an embodiment of the invention for evaluating the tear film dynamics of an eye.

FIG. 1 is a block diagram of a system 100 according to an embodiment of the invention for evaluating the tear film dynamics of an eye. Unless otherwise noted herein, "tear film dynamics" refers to the changing properties of tear film including, for example, the tear film thickness and the height of tear menisci around both upper and lower eyelids. The system 100 includes a processor 102 coupled to an OCT device 104.

The processor 102 comprises, by way of example, hardware, one or more ASICS or other substrate configurations, program logic, or software capable of representing data and instructions which operate as described herein or similar thereto. The processor 102 may also comprise controller circuitry, general purpose single-chip or multiple-chip microprocessors, digital signal processors, embedded microprocessors, microcontrollers, combinations of the foregoing, or the like. In some embodiments, the processor 102 is a conventional computer that is equipped with a conventional modem. In other embodiments, the processor 102 can be any device that allows a user to interact with the system 100 including, for example, a computer workstation, a local area network of individual computers, a personal digital assistant, a wireless communications device, a transponder, or the like.

In an embodiment, the processor 102 includes an internal memory device 106 comprising, for example, random access memory (RAM). The processor 102 can also be coupled to an external memory device 107 comprising, for example, drives that write to and read from hard and floppy disks, magnetic tape, CDs or DVDs. The internal memory device 106 or the external memory device 107, or both, can comprise program instructions 108, 109 for controlling the OCT device 104, collecting image data, generating OCT images, analyzing OCT images, measuring tear film thickness and meniscus height, performing statistical analysis on measured data, displaying OCT images or video, and other functions as described herein.

The OCT device 104 is configured to capture data in real-time for multiple OCT images between consecutive blinks of an eye. The OCT device 104 uses optical backscattering of light to produce cross-sectional images of structures. Duke University developed a customized, exemplary embodiment of the OCT device 104 that is usable for the present invention. The OCT device 104 developed by Duke University provides fast imaging of the anterior segments of the eye and uses a light source at a wavelength of approximately 1310 nm that yields improved speed and resolution as compared to typical OCT devices which use approximately 830 nm light sources.

The OCT device 104 can generate up to eight images per second or more to produce a video of the anterior segment of the eye including the tear film. The video images allow a user to view, measure and analyze the tear film thickness and menisci heights as they change with time. The OCT device 104 has a telecentric design wherein parallel light provides for wide scans to capture the spatial relationships of an ocular surface. For example, a single scan is at least wide enough (e.g., approximately 15 mm) to image both the upper meniscus and the lower meniscus at the same time.

The OCT device 104 reconstructs an OCT image from 960 single scans taken at various scan depths. The scan width is adjustable and can be determined by the area of interest. The scan depth is based at least in part on the depth of the tissue layer of interest. If needed, approximately 4000 single scans can be obtained per second from a small surface area to obtain additional structure details. Due to the fast scanning speed of the OCT device 104, dynamic changes in the tear film between blinks of an eye can be tracked and recorded in real-time.

The system 100 shown in FIG. 1 further includes an input device 110, an output device 111, a display 112, a slit lamp 114, a camera 116 and an image storage device 118. The input device 108 may include, by way of example only, an Internet or other network connection, a mouse, a keypad, other devices that allow a user to enter data into the processor 102, combinations of the foregoing, or the like. The output device 110 may include, by way of example only, a printer, an Internet or other network connection, an image or video recording device, a video display device, combinations of the foregoing, or the like. The display 112 comprises one or more video display monitors and is configured to display OCT images or video in real-time as they are generated by the OCT device 104. The display 112 is also configured to display OCT images or video stored in, for example, the memory device 106 or other storage medium.

The OCT device 104 and the camera 116 may be mounted on the slit lamp 114 to allow optical and OCT images to be acquired simultaneously. Alternatively, the OCT device 104 may comprise a hand-held probe configured to be manually positioned in proximity to an eye. The camera 116 may include, by way of example only, a film camera, a digital camera, a motion picture camera, a video camera, a digital video camera, combinations of the foregoing, or the like. As discussed in more detail below, the camera 116 is useful for comparing changes in the OCT tear film measurements with, for example, visibly observable changes in patterns created by fluorescein or other dyes placed in an eye. Thus, the OCT data can be correlated with characteristics observable in the fluorescein pattern such as tear stability as determined by the tear break up time. An image storage device 118 is coupled to the camera 118 for storing the visible images or video.

OCT Images of Tear Film Layer and Menisci

Figure 2:
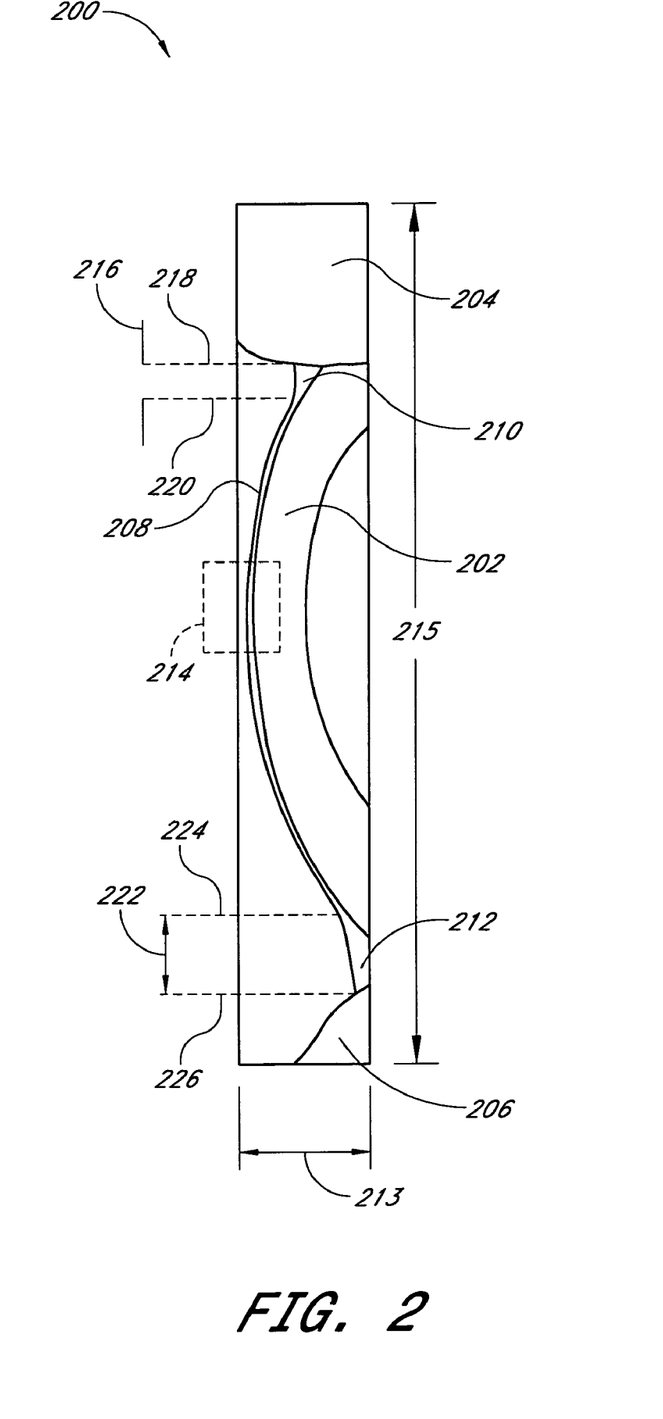
FIG. 2 is a graphical representation according to an embodiment of the invention of an OCT image.

FIG. 2 graphically represents an OCT image 200 according to an embodiment of the invention. The OCT image 200 provides a cross-sectional side view of various structures of an anterior segment of an eye. The imaged structures include a cornea 202, an upper eyelid 204, a lower eyelid 206, a tear film layer 208, an upper meniscus 210 of the tear film layer 208, and a lower meniscus 212 of the tear film layer 208. While each of these structures can be imaged separately, in a preferred embodiment, at least the tear film layer 208 at a central location 214 of the cornea 202 and both the upper meniscus 210 and the lower meniscus 212 are imaged together to provide information about the overall tear film dynamics.

The OCT image 200 comprises information from a plurality of axial scans taken across an eye. Each axial scan provides structural information in the direction of light from an OCT probe illuminating the anterior segment of the eye. Thus, each axial scan provides information in the direction of depth 213 as shown in FIG. 2. Differences in the reflectivity of the backscattered light at different depths allow the structures of the anterior segment of the eye to be distinguished from one another in the OCT image 200 shown in FIG. 2. The OCT image 200 is generated by combining a plurality of axial scans in the direction of a vertical scan line (note that this direction is represented by vertical scan line 215 in FIG. 2) extending between the upper and lower eyelid margins of an eye. Variations in reflectivity are displayed as variations in brightness or intensity in the OCT image 200. In an embodiment, variations in reflectivity are color-coded to highlight structural differences. For example, warmer colors (e.g., red, yellow, orange, etc.) may be used to show a higher reflectivity and cooler colors (e.g., blue, green, purple, etc.) may be used to show a lower reflectivity.

By way of example, the vertical scan line 215 may range from approximately 10 mm to approximately 15 mm long so that the OCT image 200 includes both the upper meniscus 210 and the lower meniscus 212. In an embodiment, the width of each axial scan is adjusted according to the selected length of the vertical scan line 215. For example, a vertical scan line 215 of approximately 12.5 mm could be generated from 960 axial scans each having a width of approximately 13 μm.

In an exemplary embodiment, approximately eight OCT images 200 are generated per second to record rapid changes to the tear film layer 208, including the upper meniscus 210 and the lower meniscus 212.

Figure 3:
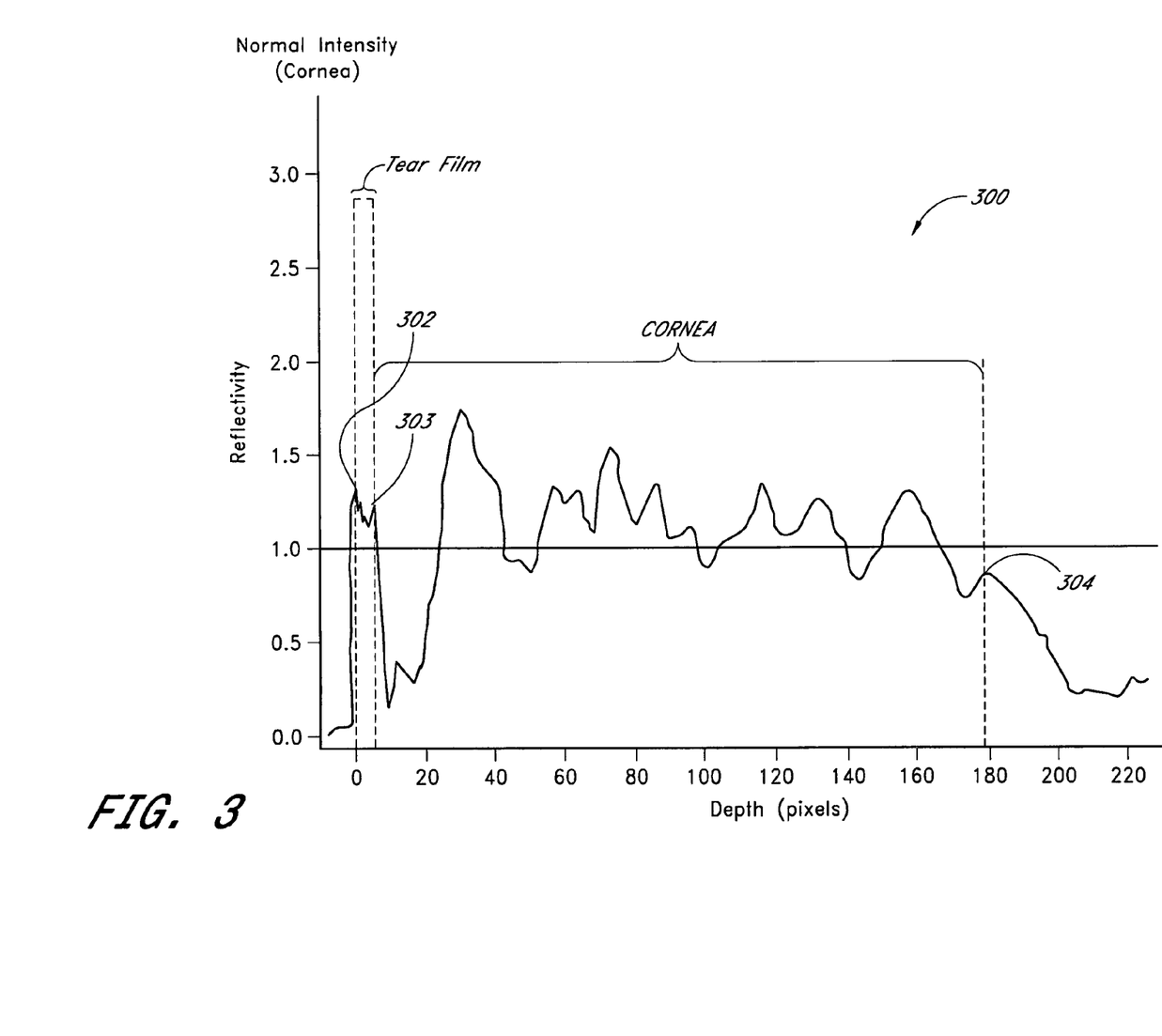
FIG. 3 is an exemplary reflectivity profile according to an embodiment of the invention of a single axial scan.

FIG. 3 illustrates a reflectivity profile 300 of a single axial scan. The reflectivity profile 300 illustrates differences in the reflectivity of backscattered light at different depths of an eye. In FIG. 3, the reflectivity is displayed as a normalized intensity of the backscattered light and the depth is shown in pixels. An artisan will recognize from the disclosure herein that the depth can also be displayed in units of length (e.g., microns, etc.). The resolution of the axial scan is defined by the pixels per unit length.

Differences in reflectivity of backscattered light at different depths allow the structures of the anterior segment of the eye to be quantitatively measured. For example, a first peak 302 shown in the reflectivity profile 300 corresponds to an interface between air and a tear film layer. In FIG. 3, the first peak 302 is used as a reference point and corresponds to a depth of zero pixels. A second peak 303 corresponds to the interface between the tear film layer and the anterior surface of a cornea. A third peak 304 corresponds to the posterior surface of the cornea. Thus, the thickness of the tear film layer can be derived from the distance between the first peak 302 and the second peak 303. Similarly, the thickness of the cornea can be derived from the distance between the second peak 303 and the third peak 304.

Image Processing of Tear Meniscus Height

Referring again to FIG. 2, the height of the upper meniscus 210 and the lower meniscus 212 can be measured from the same OCT image 200. The height of the upper meniscus 210 is measured by analyzing a vertical distance 216 (hereinafter, the "upper meniscus height 216") between upper and lower vertical limits of the upper meniscus 210. In an embodiment, a user defines the upper and lower vertical limits of the upper meniscus 210 by placing software-controlled cursors 218, 220 at the upper and lower limits, respectively. The software that controls the cursors 218, 220 is configured to determine the vertical separation in pixels between the cursors 218, 220. The software is also configured to convert the separation in pixels to units of length (e.g., microns) to determine the physical upper meniscus height 216. The conversion is based on the vertical resolution (i.e., pixels per unit length) of the OCT image 200.

Similarly, the height of the lower meniscus 212 is measured by analyzing a vertical distance 222 (hereinafter, the "lower meniscus height 222") between upper and lower vertical limits of the lower meniscus 206. In an embodiment, the user defines the upper and lower limits of the lower meniscus 212 by placing software-controlled cursors 224, 226 at the upper and lower limits, respectively. The software is configured to determine the vertical separation in pixels between cursors 224, 226 and to determine the physical lower meniscus height 218.

An artisan will recognize from the disclosure herein that the OCT image 200 is not drawn to scale. However, by way of exemplary measurements and to provide a sense of the relative values for the measurements described above with respect to the OCT image 200, the upper meniscus height 216 is approximately 390 μm and the lower meniscus height 222 is approximately 1,367 μm. These exemplary results were obtained approximately five minutes after artificial tears were dropped into an eye of a test subject and are for illustrative purposes only, and not for limitation.

Image Processing of Tear Film Layer Thickness

The thickness of the tear film layer 208 can be accurately measured from one or more OCT images 200. In an embodiment, a single axial scan corresponding to the central location 214 of the cornea is analyzed to determine the thick of the tear film layer. For example, as discussed above in relation to FIG. 3, the distance between the first peak 302 and the second peak 303 of the reflectivity profile 300 can be can be converted from pixels to a unit of measurement corresponding to the thickness of the tear film layer 208. In other embodiments, multiple axial scans corresponding to the central location 214 of the cornea 202 are averaged together to determine the thickness of the tear film layer 208. In an exemplary embodiment, approximately twenty axial scans in the central location 214 are averaged together to determine the thickness of the tear film layer 208.

In some embodiments, it is preferable to measure the thickness of the tear film layer 208 in the area of the central location 214 where the tear film layer 208 is generally the thickest (except for at the menisci 210, 212). Further, the tear film layer 208 in the central location 214 is substantially perpendicular to incident light from an OCT probe. However, an artisan will recognize from the disclosure herein that the present invention is not so limited. In fact, the tear film layer 208 can be measured at any location including, for example, at the menisci 210, 212.

Figure 4:
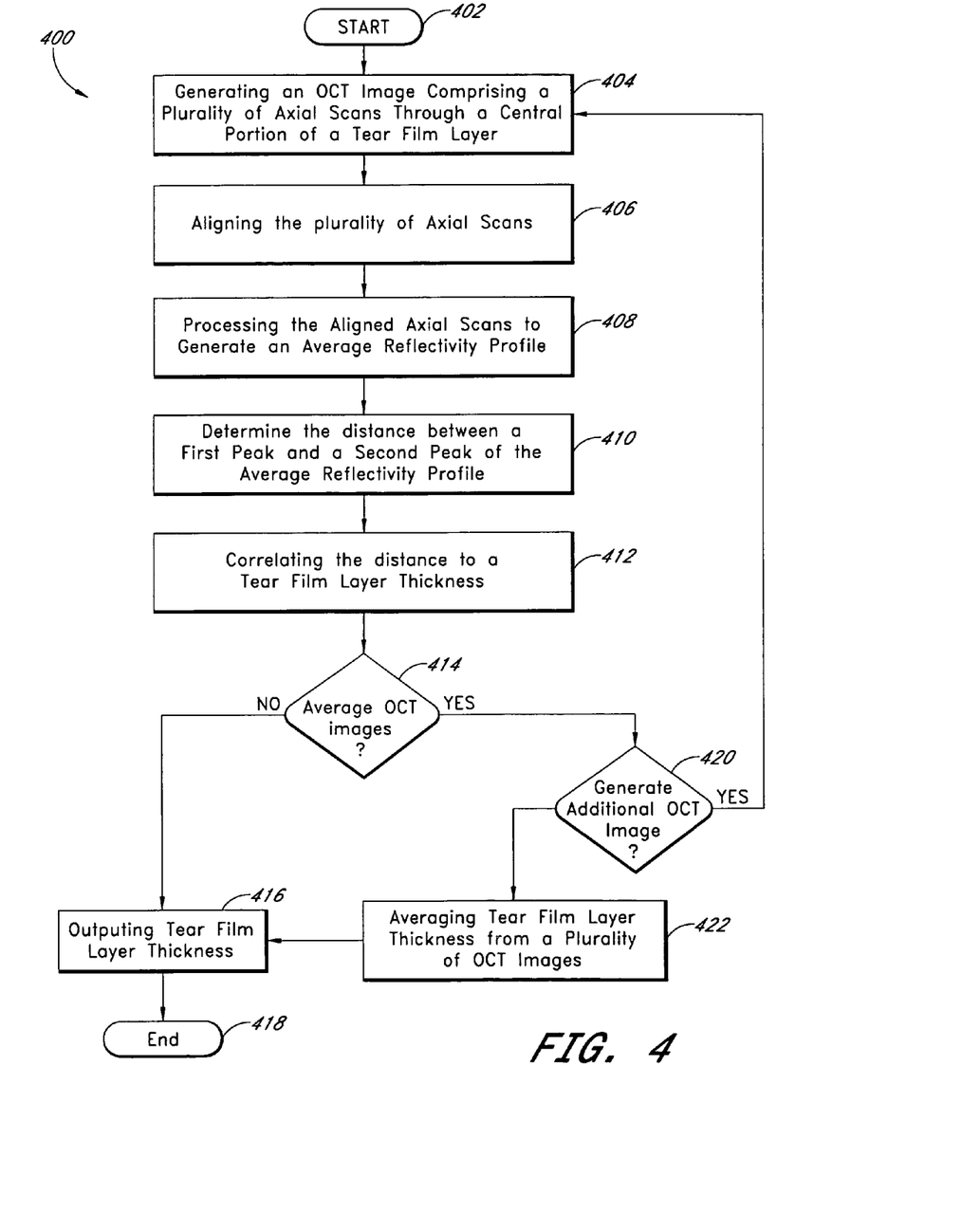
FIG. 4 is a flow chart according to an embodiment of the invention illustrating portions of a process for measuring tear film thickness.
Figure 5A:
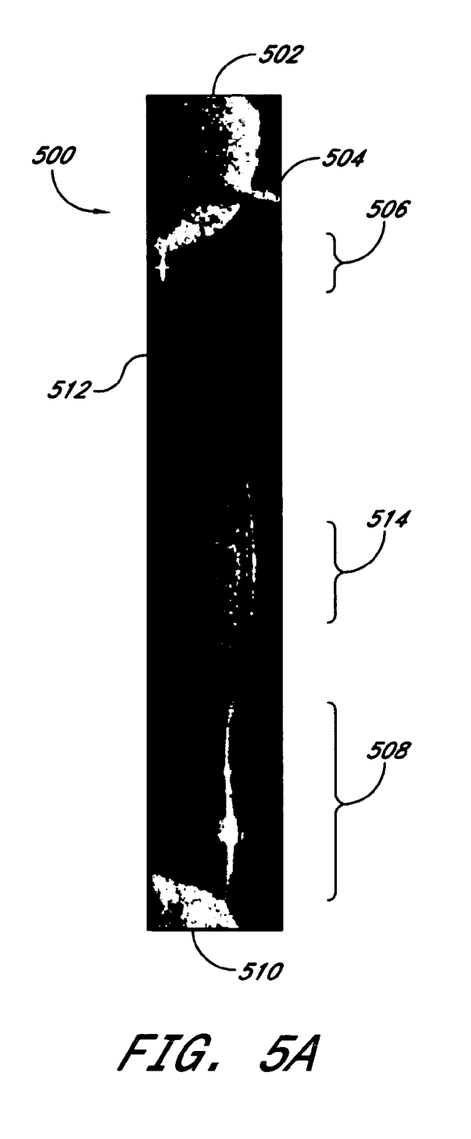
FIGS. 5A and 5B are exemplary OCT images according to embodiments of the invention.
Figure 6:
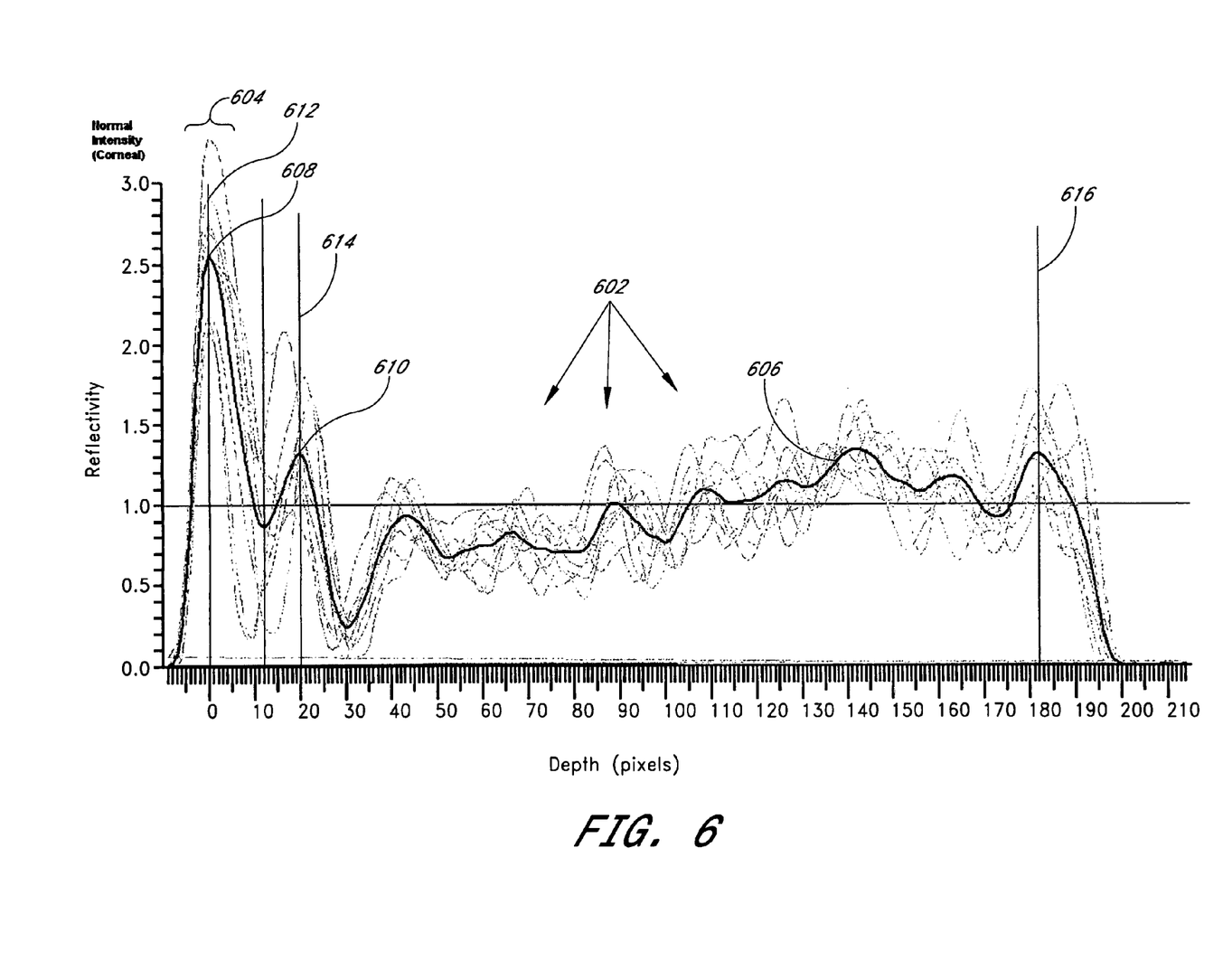
FIG. 6 is a plurality of exemplary reflectivity profiles according to an embodiment of the invention.

FIG. 4 is a flow chart illustrating portions of a process 400 for measuring tear film thickness according to an embodiment of the invention. For illustrative purposes, the process 400 shown in FIG. 4 will be discussed with reference to FIGS. 5A and 6. FIG. 5A illustrates an OCT image 500 generated by the process 400 shown in FIG. 4. FIG. 6 illustrates reflectivity profiles 602 (shown as faded waveforms) corresponding to a plurality of axial scans usable to generate the OCT image 500 shown in FIG. 5A.

The process 400 starts in a block 402. In a block 404, the process 400 comprises generating the OCT image 500 comprising a plurality of axial scans through a central portion of a tear film layer. Various physical structures are distinguishable in the OCT image 500 including an upper eyelid 502, eyelashes 504, an upper tear meniscus 506, a lower tear meniscus 508, a lower eyelid 510, a cornea 512, and a tear film layer 514 in the central area of the cornea 512 (hereinafter, the central tear film layer 514).

The plurality of reflectivity profiles 602 shown in FIG. 6 correspond to the plurality of axial scans through the central tear film layer 514. As discussed above, the OCT image 500 preferably comprises many axial scans along a scan line from an upper eyelid to a lower eyelid. However, the process 400 in the block 402 is concerned with the plurality of axial scans taken approximately halfway between the upper eyelid and the lower eyelid.

The plurality of axial scans corresponding to the central tear film layer 514 is extracted from the axial scans that make up the entire OCT image 500. In an alternative embodiment, the OCT image 500 comprises only the plurality of axial scans corresponding to the central tear film layer 514 and extraction is not used. In another alternative embodiment, the plurality of axial scans corresponding to the central tear film layer 514 is separately stored or processed in real-time as the OCT image 500 is being generated. In an exemplary embodiment, twenty axial scans at a substantially central location with respect to the cornea are used.

In a block 406, the process 400 includes aligning the plurality of axial scans corresponding to the central tear film layer 514. As shown in FIG. 5A, the central tear film layer 514 is curved. Thus, the distance from the OCT probe to the interface between the air and the outer surface of the central tear film layer 514 will be different for each of the plurality of axial scans. As discussed below, aligning the interface between the air and the outer surface of the central tear film layer 514 allows the plurality of axial scans to be analyzed together to increase the accuracy of the measurement.

As shown in FIG. 6, respective first peaks 604 of the plurality of reflectivity profiles 602 have been aligned with respect to one another. The respective first peaks 604 correspond to an interface between air and the tear film layer. Thus, the respective first peaks 604 are aligned and used as a reference for measuring the depth of structures such as the thickness of the central tear film layer 514 and the anterior and posterior surfaces of the cornea 512. Accordingly, as shown in FIG. 6, the aligned first peaks 604 define a depth of zero pixels.

In a block 408, the process 400 further includes processing the aligned axial scans to generate an average reflectivity profile 606, as shown in FIG. 6. Once the reflectivity profiles 602 have been aligned, they can be averaged pixel by pixel to generate the average reflectivity profile 606. Averaging the reflectivity profiles 602 reduces measurement errors caused by minor deviations found in any particular one of the reflectivity profiles 602.

In a block 410, the process 400 includes determining a distance between a first peak 608 and a second peak 610 of the average reflectivity profile 606. To measure the distance between the first peak 608 and the second peak 610, a first software controlled cursor 612 is placed at the first peak 608 and a second software controlled cursor 614 is placed at the second peak 610. The software controlled cursors 612, 614 can be placed manually by a user or automatically by the software using, for example, a maximum or peak search algorithm. The software controlled cursors 612, 614 are configured to respectively indicate the depth in pixels of the first peak 608 and the second peak 610. Thus, the distance between the first peak 608 and the second peak 610 is determined by subtracting the location indicated by the second cursor 614 from the location indicated by the first cursor 612.

In a block 412, the process 400 includes correlating the distance between the first peak 608 and the second peak 610 to a tear film layer thickness (i.e., the average thickness of the central tear film layer 514). The first peak 608 corresponds to the interface between air and the outer surface of the central tear film layer 514. The second peak 610 corresponds to the difference between the inner surface of the central tear film layer 514 and the anterior surface of the cornea 512. Thus, the difference between the first peak 608 and the second peak 610 corresponds to the average thickness of the central tear film layer 514. The depth in pixels between the first software controlled cursor 612 and the second software controlled cursor 614 is converted to a physical distance measurement with units of length, as discussed above.

As discussed above, approximately eight OCT images can be generated per second by the OCT device 104 shown in FIG. 1. In some embodiments of the invention, tear film thickness measurements obtained from a plurality of OCT images can be combined to increase the accuracy of the overall measurement. In a block 414, the process 400 queries whether to average a plurality of OCT images to determine the tear film layer thickness. If no, at a block 416, the process 400 includes outputting the tear film layer thickness 416 determined in the block 412 and the process 400 ends in a block 418.

If it is determined in the block 414 that a plurality of OCT images are to be averaged, in a block 420 the process 400 queries whether to generate an additional OCT image. If yes, the process 400 repeats the block 404 to generate the additional OCT image. The process 400 also repeats the blocks 406, 408, 410, 412 to determine a tear film thickness layer corresponding to the additional OCT image. In a block 422, the process 400 includes averaging the tear film layer thickness measurements obtained from the plurality of OCT images. In the block 416, the process 400 includes outputting the tear film layer thickness determined in the block 422 and the process 400 ends in the block 418.

Figure 5B:
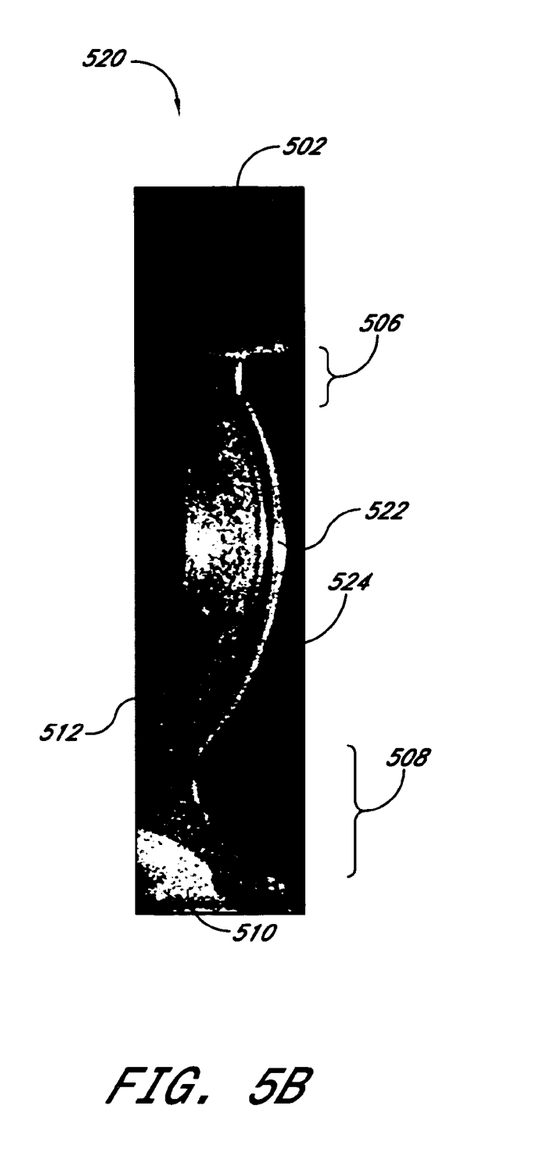

While the process 400 illustrated in FIG. 4 has been described with reference to FIGS. 5A and 6 to measure tear film thickness, other embodiments will occur to those skilled in the art. For example, FIG. 5B illustrates an OCT image 520 generated by the system 100 shown in FIG. 1 that is usable to analyze the effect of contact lens use on tear dynamics. Various physical structures are distinguishable in the OCT image 520 including an upper eyelid 502, an upper tear meniscus 506, a lower tear meniscus 508, a lower eyelid 510, a cornea 512, a pre-lens tear film layer 522, and a contact lens 524 between the cornea 512 and the pre-lens tear film layer 522.

The OCT image 520 can be used to measure the heights of the upper meniscus 506 and the lower meniscus 508 as discussed above with respect to FIGS. 2 and 3. In addition, or in other embodiments, the process 400 discussed with respect to FIG. 4 can be used to measure the thickness of the distinguishable structures shown in FIG. 5B including the upper meniscus 506, the lower meniscus 508, the pre-lens tear film layer 244, the contact lens 524, the cornea, other distinguishable features, or combinations of the foregoing.

Analysis of Tear Dynamics

Changes in the tear film thickness and upper and lower tear film menisci between blinks are highly correlated with clinical symptoms such as feelings of dryness, irritation, or the like. Thus, the ability to analyze tear dynamics in real time has many applications including diagnosis of diseases and disorders (e.g., dry eye syndrome). Analyzing the rapid changes in tear film dynamics also provides valuable insights into the effects of common treatments for dry eye, including artificial tears to "thicken" the tear film, punctal occlusion to increase the quantity of the tear film, and treatment of meibomian gland disease to improve the quality of the tear film.

Thus, the systems and methods of the present invention can be used, for example, to characterize tear dynamics and their relationships with tear stability and ocular comfort. Measuring rapid changes in tear dynamics can also be used, for example, to analyze the manipulation of tears, the effect of hard or soft contact lens usage, the effect of environmental factors, or combinations of the foregoing. The following exemplary embodiments illustrate analyses of tear film dynamics to diagnose and treat diseases and disorders. However, analysis of tear film dynamics is not limited to the following exemplary embodiments. Rather, an artisan will recognize from the disclosure herein many other uses for measuring rapid changes in the tear film thickness and upper and lower tear film menisci.

Figure 7A:
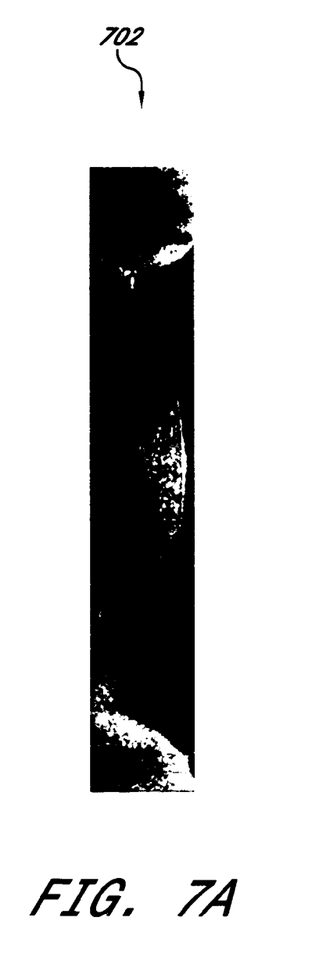
FIGS. 7A-7C are exemplary OCT images according to an embodiment of the invention.
Figure 7B:
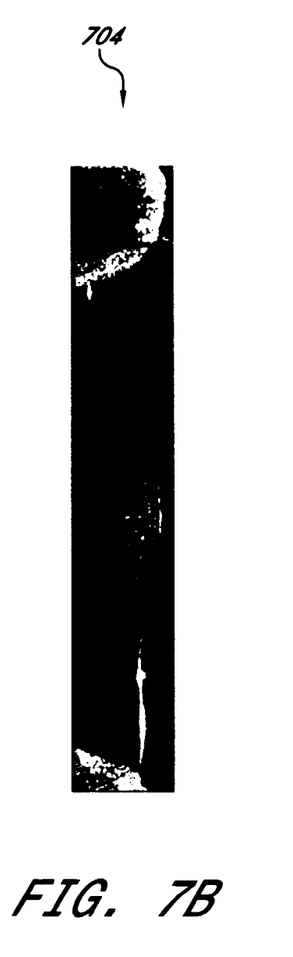
Figure 7C:
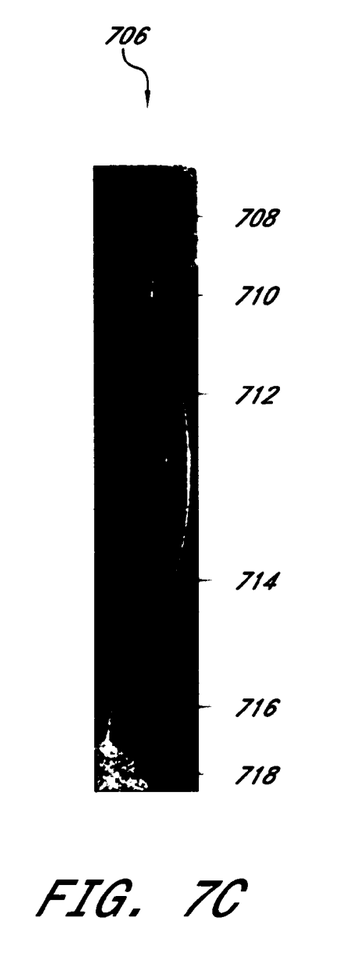

FIGS. 7A-7C are photographs of three OCT images 702, 704, 706 or frames taken from an OCT image video according to an exemplary embodiment of the invention. As discussed above, the OCT device 104 provided by Duke University is configured to generate a video of up to eight or more OCT images per second. The OCT images 702, 704, 706 form part of such an OCT image video that allows a user to view and analyze real-time changes in tear film dynamics. The OCT images 702, 704, 706 each illustrate an upper eyelid 708, an upper tear meniscus 710, a cornea 712, a tear film layer 714 covering the cornea 712, a lower tear meniscus 716, and a lower eyelid 718.

The OCT images 702, 704, 706 were generated from a vertical OCT scan of an eye. The vertical OCT scan was approximately 12.5 mm long. The OCT image 702 shown in FIG. 7A was generated after a full blink of the eye and before the application of a drop of artificial tears. Note that the tear film layer 714 shown in FIG. 7A is too thin to visually differentiate from the cornea 712. From the OCT image 702, the thickness of the cornea 712 plus the tear film layer 714 was measured as described above to be approximately 563.2 µm.

The OCT image 704 shown in FIG. 7B was generated after one drop of an artificial tear was placed in the eye. The OCT image 704 shows the increase of the tear film thickness 714 as well as the heights of both the upper meniscus 710 and the lower meniscus 716. From the OCT image 704, the thickness of the cornea 712 was measured as described above to be approximately 556.8 µm. By subtracting the thickness of the cornea 712 obtained from the OCT image 704 from the thickness of the cornea 712 plus tear film layer 714 obtained from the OCT image 702, the thickness of the tear film layer 714 before the application of the eye drop was determined to be approximately 6.4 µm after the blink in FIG. 7A.

The OCT image 706 shown in FIG. 7C was generated approximately five minutes after the application of the eye drop. The OCT image 706 shows the partial recovery of the original (i.e., before the application of the eye drop) thickness of the tear film layer 714 as well as the heights of the upper tear meniscus 710 and the lower tear meniscus 716. This recovery is effected by factors such as temperature, humidity and the ability of the eye to maintain a dynamic equilibrium among production, drainage and evaporation. Thus, the OCT image video from which the OCT images 702, 704, 706 were taken can be used evaluate these factors and diagnose, for example, dry eye syndrome or its cause.

Tear film dynamics can also be effected by the formulation of the artificial tear placed in the eye. Different types of artificial tears may increase tear volume for different periods of time, be distributed differently over the eye over time, or effect the production, drainage or evaporation of tears differently. Thus, the OCT image video from which the OCT images 702, 704, 706 were taken can be used to analyze the properties and effectiveness of different types of artificial tears or other types of treatments such as punctal occlusion.

From the OCT image 706, the thickness of the central tear film layer 714 was measured as described above to be approximately 16 µm. Thus, after approximately five minutes, the tear film layer 714 was approximately 9.6 µm thicker than before the application of the eye drop. At approximately eight frames per second, the OCT image video from which the OCT images 702, 704, 706 were taken can be used to evaluate changes in tear film that occur over long periods of time (i.e., minutes, hours, etc.) or relatively short periods of time between successive blinks of an eye. It is estimated that the thickness of the tear film layer 714 can change by approximately 2.5 µm within two to four seconds after blinking. These rapid changes can be measured to diagnose disease or disorder or to evaluate the effectiveness of treatment.

Figure 8A:
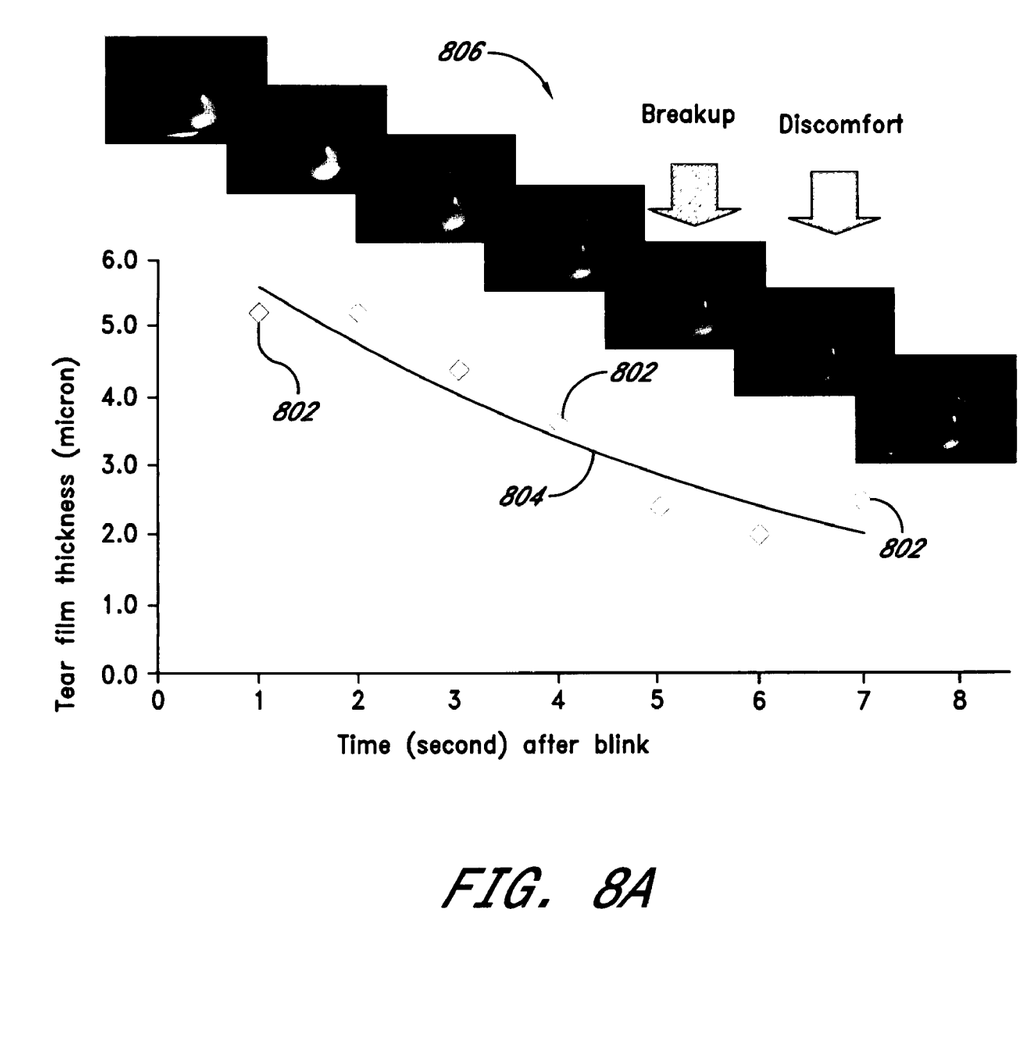
FIG. 8A is an exemplary graph and slit lamp video images according to an embodiment of the invention that illustrate the relationship between rapid changes in tear film thickness and tear film breakup.
Figure 8B:
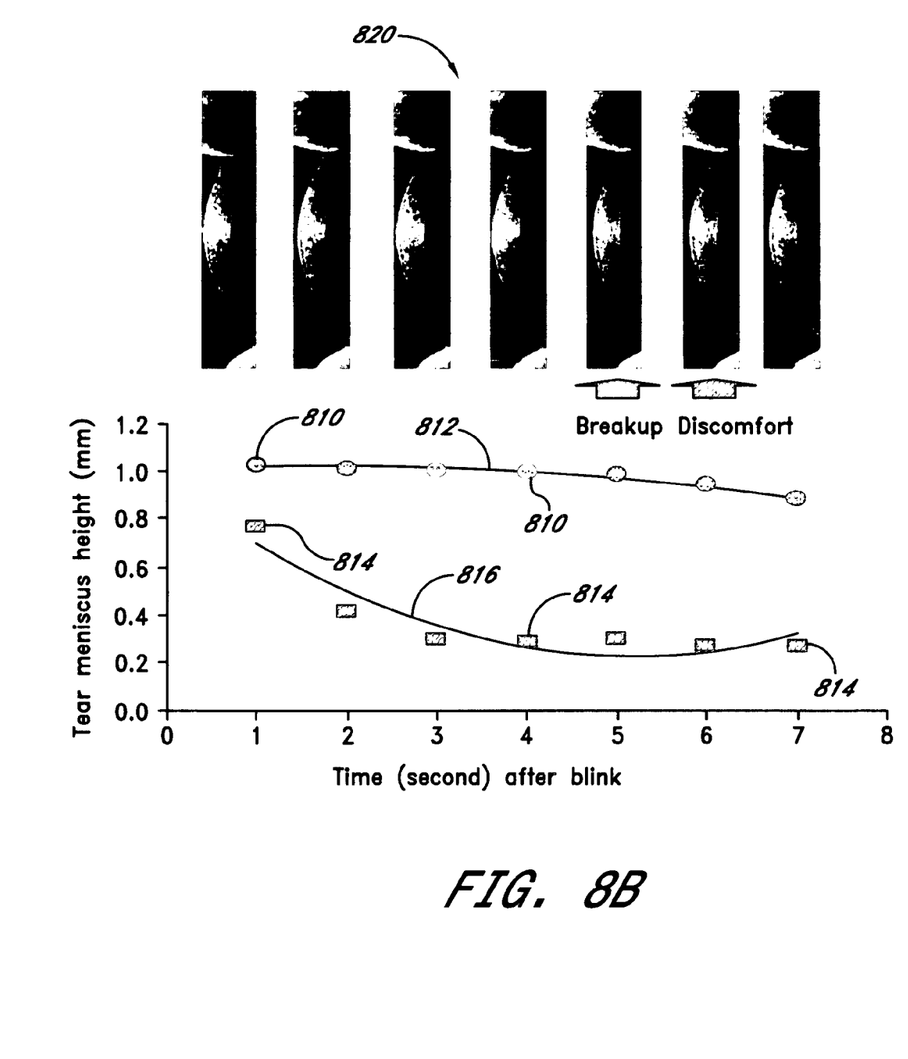
FIG. 8B is an exemplary graph and OCT video images according to an embodiment of the invention that illustrate the relationship between the rapid changes in the height of tear menisci and tear film breakup.

FIGS. 8A and 8B are exemplary graphs illustrating the relationship between rapid changes in tear film characteristics and tear film breakup. Tear film breakup provides an indication of tear stability and occurs when the tear film no longer covers the cornea in a continuous layer. The tear film can be redistributed over the cornea in a continuous layer by blinking. However, low tear stability will cause the tear film layer to breakup again. Tear film breakup can cause discomfort, pain, damage to the eye such as ulceration of the cornea, and loss of vision.

As mentioned above, tear film breakup can be observed by placing fluorescein or other dyes in the eye to stain the tear film layer. In the exemplary embodiment shown in FIGS. 8A and 8B, the camera 116 attached to the slit lamp 114 shown in FIG. 1 is used to video record observable changes to a fluorescein stained eye of a subject while the tear film dynamics are measured using the OCT device 104. Thus, the tear film breakup observed in the slit lamp video images can be correlated with changes in tear film thickness, upper meniscus height, lower meniscus height, or a combination of the foregoing. Since tear breakup can occur rapidly and the tear film layer is redistributed after each blink, at least two OCT measurements are taken between consecutive blinks to determine changes in tear film dynamics.

FIG. 8A illustrates an exemplary graph 804 showing changes in the central tear film thickness over time. For illustrative purposes, seven slit lamp video images 806 are shown above the graph 804 corresponding to the time, in seconds, after a blink of the eye. As shown in this example, the cornea (shown as dark areas beneath the fluorescein in the slit lamp video images 806) becomes more and more visible as the fluorescein stained tear film layer thins and eventually breaks at approximately five seconds after blinking. As also indicated in this example, the subject reported discomfort in the eye approximately six seconds after blinking.

FIG. 8A illustrates data points 802 (seven shown) corresponding to OCT tear film thickness measurements generated at approximately every second after the blink. The respective tear film thickness of each data point 802 is plotted versus time. The graph 804 showing the changes to the tear film thickness over time is an approximation of the data points 802. Many possible approximation methods can be used to generate the graph 804 from the data points 802. In an embodiment, the graph 804 is a least squares fit of the data points 802. As shown in this example, the measured tear film thickness at the tear breakup time (i.e., approximately five seconds) is approximately 2.5 µm and the graph 802 indicates approximately 2.8 µm of tear film thickness.

FIG. 8B illustrates an exemplary graph 812 showing changes in the lower meniscus height over time and an exemplary graph 816 showing changes in the upper meniscus height over time. For illustrative purposes, seven OCT video images 820 are shown above the graphs 812, 816 corresponding to the time after the blink of the eye. The graph 804 of the central tear film thickness shown in FIG. 8A and the graphs 812, 814 of the respective meniscus heights shown in FIG. 8B are generated from the OCT video images 820 in the manner described above. For reference, the breakup time of approximately five seconds and the reported discomfort of approximately six seconds are indicated in FIG. 8B.

FIG. 8B illustrates data points 810 (seven shown) corresponding to OCT measurements of the lower meniscus height generated at approximately every second after the blink. The respective height of each data point 810 is plotted versus time. The graph 812 showing the changes to the lower meniscus height is an approximation of the data points 810. FIG. 8B also illustrates data points 814 (seven shown) corresponding to OCT measurements of the upper meniscus height generated at approximately every second after the blink. The respective height of each data point 814 is plotted versus time. The graph 816 showing the changes to the upper meniscus height is an approximation of the data points 810. In an embodiment, the graph 812 is a least squares fit of the data points 810 and the graph 816 is a least squares fit of the data point 814.

As shown in this example, the graph 816 of the upper meniscus height varies from approximately 0.8 mm to approximately 0.3 mm, while the graph 812 of the lower meniscus height remains relatively stable at approximately 1.0 mm. FIGS. 8A and 8B illustrate that the variations and relationships of the tear film thickness and tear menisci can be analyzed over time between consecutive blinks of the eye, providing advantageous diagnostic and treatment evaluation capabilities.

Figure 9A:
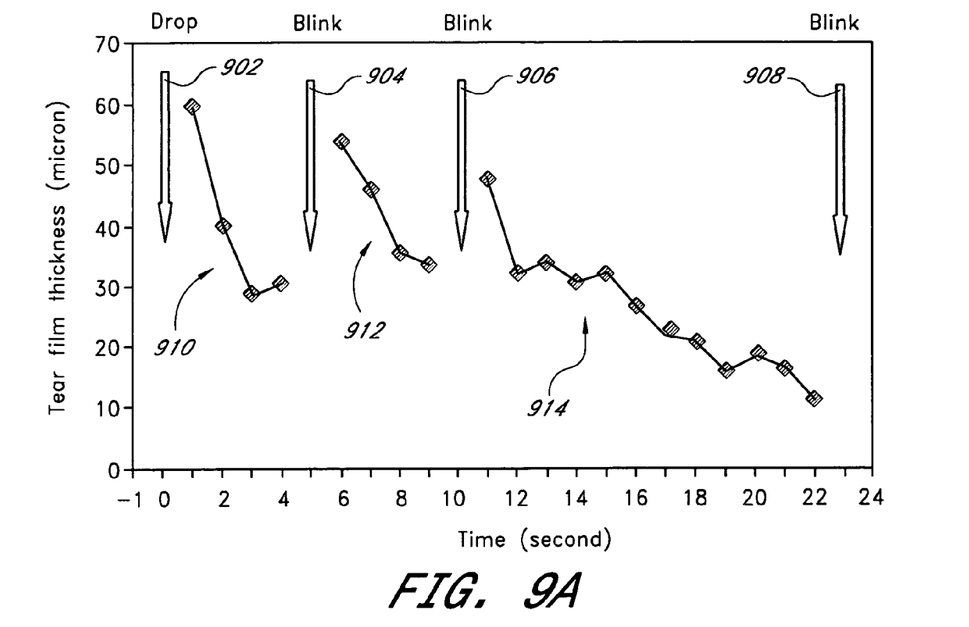
FIGS. 9A and 9B are exemplary graphs according to an embodiment of the invention of tear film dynamics measured over a plurality of blinks of an eye to analyze the effect of an artificial tear placed in the eye.
Figure 9B:
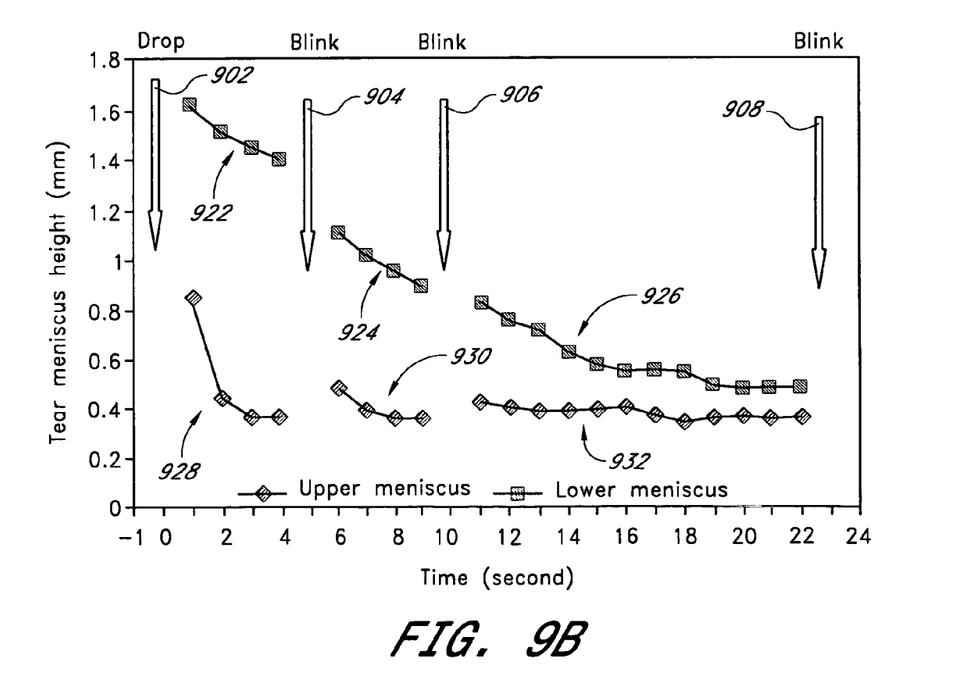

FIGS. 9A and 9B are exemplary graphs of tear film dynamics measured over a plurality of blinks of an eye to analyze the effect of an artificial tear placed in the eye. As discussed above, artificial tears are used to "thicken" the tear film or otherwise treat eye diseases or disorders. The effect of different types of artificial tears can be analyzed by measuring the tear film dynamics two or more times between consecutive blinks as well as before and after a blink.

Approximately eight OCT images are generated per second and analyzed to determine the thickness of the central tear film and the heights of the menisci over time. An initial OCT measurement of the tear film dynamics is taken after a blink and before a drop of artificial tears is instilled into the conjunctival sac of the eye. The initial measurement establishes a baseline for analyzing the subsequent OCT measurements. In this example, the tear film thickness has a baseline of approximately 6.2 µm, the upper meniscus height has a baseline of approximately 0.28 mm, and the lower meniscus height has a baseline of approximately 0.30 mm. After the drop is instilled, the tear film dynamics are repeatedly measured during several consecutive blinks of the eye.

As shown in FIGS. 9A and 9B, the drop of artificial tears is instilled at a drop time 902 that is used as a reference. A first blink of the eye occurs at a first blink time 904 of approximately five seconds after the drop time 902. A second blink of the eye occurs at a second blink time 906 of approximately ten seconds after the drop time 902. A third blink occurs at a third blink time 908 of approximately 23 seconds after the drop time 902.

FIG. 9A illustrates changes in tear film thickness over time. FIG. 9A shows a first plot 910 of data points (four shown), a second plot 912 of data points (four shown) and a third plot of data points (twelve shown). Each plot 910, 912, 914 corresponds to respective OCT tear film thickness measurements generated approximately every second. The first plot 910 shows the change in tear film thickness between the drop time 902 and the first blink time 904. The second plot 912 shows the change in tear film thickness between the first blink time 904 and the second blink time 906. The third plot 914 shows the change in tear film thickness between the second blink time 906 and the third blink time 908.

After the manipulation of the tear film by instilling the artificial tear at the drop time 902, the tear film thickness increases from the baseline of approximately 6.2 µm to approximately 60.0 µm. However, the first plot 910 shows that the tear film thickness quickly decreases. Also, the tear film thickness increases immediately after the first blink time 904 and the second blink time 906, followed again by decreases. The increase after the second blink time 906 is not as great as the increase after the first blink time 904, and the tear film thickness appears to be progressively returning to the baseline measurement. After approximately 22 seconds from the drop time 902, the tear film thickness is approximately 10 µm. Thus, the tear film thickness decreases as a function of time and as a function of blinking.

FIG. 9B illustrates changes in the upper and lower menisci over time. For the lower meniscus, FIG. 9B shows a first plot 922 of data points (four shown), a second plot 924 of data points (four shown) and a third plot 926 of data points (twelve shown). Each plot 922, 924, 926 corresponds to respective OCT measurements of the lower meniscus height. The first plot 922 shows the change in lower meniscus height between the drop time 902 and the first blink time 904. The second plot 924 shows the change in lower meniscus height between the first blink time 904 and the second blink time 906. The third plot 926 shows the change in lower meniscus height between the second blink time 906 and the third blink time 908.

For the upper meniscus, FIG. 9B shows a first plot 928 of data points (four shown), a second plot 930 of data points (four shown) and a third plot 932 of data points (twelve shown). Each plot 928, 930, 932 corresponds to respective OCT measurements of the upper meniscus height. The first plot 928 shows the change in upper meniscus height between the drop time 902 and the first blink time 904. The second plot 930 shows the change in upper meniscus height between the first blink time 904 and the second blink time 906. The third plot 932 shows the change in upper meniscus height between the second blink time 906 and the third blink time 908.

After the manipulation of the tear film by instilling the artificial tear at the drop time 902, the lower meniscus height increases from the baseline of approximately 0.30 mm to approximately 1.62 mm, and the upper meniscus height increases from the baseline of approximately 0.28 mm to approximately 0.85 mm. However, the respective first plots 922, 928 show that the lower and upper meniscus heights quickly decrease. The heights decrease as a function of time between blinks and as a function of blinking. Although not shown, it has been observed that different types of artificial tears produce different patterns of decreasing menisci. Overall, the lower meniscus tends to maintain a greater height than the upper meniscus.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method of imaging a tear film layer of an eye, the method comprising:
    acquiring a plurality of optical coherence tomographic images of said eye between consecutive blinks of said eye, said tomographic images depicting a cross-section of a full thickness of a cornea and a full thickness of the tear film layer of the eye and further depicting an upper tear meniscus and a lower tear meniscus of the eye;
    wherein said plurality of said tomographic images depict said tear film layer as distinct from the cornea of said eye.

2. The method of claim 1, wherein at least one of said tomographic images depicts a contact lens as distinct from said cornea of said eye.

3. The method of claim 2, wherein said at least one of said tomographic images depicts a pre-lens tear film layer as distinct from said contact lens and said cornea of said eye.

4. The method of claim 3, further comprising measuring a thickness of at least one of said contact lens and said pre-lens tear film layer.

5. The method of claim 1, further comprising measuring a thickness of said tear film layer.

6. The method of claim 5, wherein measuring said thickness of said tear film layer comprises measuring said thickness multiple times over time.

7. The method of claim 6, wherein measuring said thickness of said tear film layer comprises:
    processing data from a first image of said tomographic images to generate an average reflectivity profile;
    determining a distance between a first peak and a second peak of said average reflectivity profile, wherein said first peak corresponds to an interface between air and said tear film layer, and wherein said second peak corresponds to an interface between the tear film layer and said cornea; and
    correlating said distance between said first peak and said second peak to a first thickness of said tear film layer.

8. The method of claim 7, further comprising averaging said first thickness obtained from said first image with a second thickness obtained from a second image of said tomographic images.

9. A method of imaging a tear film layer of an eye, the method comprising:
    acquiring a plurality of images of said eye between consecutive blinks of said eye;
    wherein, the plurality of images depict a full thickness of the tear film layer as distinct from the cornea of said eye, and depict an upper tear film meniscus and a lower tear film meniscus as distinct from the cornea of said eye.

10. A method of imaging an eye, the method comprising:
    measuring with an instrument a cross-sectional thickness of a tear film layer of said eye at least twice between consecutive blinks of said eye, wherein said instrument does not physically contact said eye during said measuring.

11. The method of claim 10, further comprising measuring a reflectivity of said tear film layer.

12. A method of imaging an eye, the method comprising:
measuring with an instrument a cross-sectional meniscus height of a tear film of said eye at least twice between consecutive blinks of said eye, wherein said instrument does not physically contact said eye during said measuring.

13. A system for evaluating a tear film layer of an eye, the system comprising:
an optical coherence tomography device configured to acquire at least two images of said tear film layer between consecutive blinks of said eye, said tomographic images depicting a cross-section of a full thickness of a cornea and a full thickness of the tear film layer of the eye, and further depicting an upper tear meniscus and a lower tear meniscus of the eye; and
an executable program configured to process said at least two images acquired by said optical coherence tomography device;
wherein said executable program is further configured to determine a thickness of said tear film layer.

14. The system of claim 13, wherein hardware comprises said executable program.

15. The system of claim 13, wherein software comprises said executable program.

16. A system for evaluating a tear film layer of an eye, the system comprising:
means for acquiring at least two images of said tear film layer between consecutive blinks of said eye, said images depicting a cross-section of a full thickness of a cornea and a full thickness of the tear film layer of the eye, and further depicting an upper tear meniscus and a lower tear meniscus of the eye; and
means for determining a thickness of said tear film layer.

17. A diagnostic device comprising an optical coherence tomography system configured to measure a full cross-sectional thickness of a tear film layer of an eye at least twice between consecutive blinks of said eye.

18. A diagnostic device comprising an optical coherence tomography system configured to measure a cross-sectional thickness of an upper tear film meniscus and a lower tear film meniscus of an eye at least twice between consecutive blinks of said eye.

19. A method of imaging an eye, the method comprising measuring a full cross-sectional thickness of a tear film layer of said eye at least twice between consecutive blinks of said eye.

20. A method of imaging an eye, the method comprising measuring a cross-sectional thickness of an upper tear film meniscus and a lower tear film meniscus of said eye at least twice between consecutive blinks of said eye.

* * * * *

UNITED STATES PATENT AND TRADEMARK OFFICE
CERTIFICATE OF CORRECTION

| | | |
|---|---|---|
| PATENT NO. | : 7,281,801 B2 | Page 1 of 1 |
| APPLICATION NO. | : 10/941249 | |
| DATED | : October 16, 2007 | |
| INVENTOR(S) | : Jianhua Wang | |

It is certified that error appears in the above-identified patent and that said Letters Patent is hereby corrected as shown below:

IN THE COVER PAGE:

(56) References Cited - Other Publications:

Add --KUNIO MARUYAMA, ET AL., "Effect of Environmental Conditions on Tear Dynamics in Soft Contact Lens Wearers," Investigative Ophthalmology & Visual Science, August 2004, Vol. 45, No. 8, pp 2563-2568--

Signed and Sealed this
Seventeenth Day of January, 2012

David J. Kappos
*Director of the United States Patent and Trademark Office*